United States Patent
Li et al.

(10) Patent No.: US 7,141,721 B2
(45) Date of Patent: Nov. 28, 2006

(54) ENOYL-ACP REDUCTASES

(75) Inventors: Chun Ping Li, Johnston, IA (US); Alan R. Rendina, Wilmington, DE (US)

(73) Assignees: E. I. du Pont de Nemours and Company, Wilmington, DE (US); Pioneer Hi-Bred International, Inc., Des Moines, IA (US)

( * ) Notice: Subject to any disclaimer, the term of this patent is extended or adjusted under 35 U.S.C. 154(b) by 473 days.

(21) Appl. No.: 10/187,764

(22) Filed: Jul. 2, 2002

(65) Prior Publication Data

US 2003/0115625 A1 Jun. 19, 2003

Related U.S. Application Data

(60) Provisional application No. 60/303,309, filed on Jul. 6, 2001.

(51) Int. Cl.
 *A01H 5/00* (2006.01)
 *C12N 15/82* (2006.01)
 *C07H 21/04* (2006.01)

(52) U.S. Cl. .................. 800/298; 800/281; 536/23.6; 435/320.1; 435/440

(58) Field of Classification Search ............... 800/278, 800/281, 298; 435/320.1, 440; 536/23.2, 536/23.6
See application file for complete search history.

(56) References Cited

OTHER PUBLICATIONS de Boer et al, Database GenEMBL Accession AJ003025, Nov. 30, 1997.*
Parikh et al, Biochemistry 38: 13623-13634, 1999.*
Mou et al, The Plant Cell 12: 405-417, Mar. 2000.*
Zhonglin Mou et al., Deficiency in Fatty Acids Synthase leads to Premature Cell Death and Dramatic Alterations in Plant Morphology, The Plant Cell, vol. 12:405-417, Mar. 2000.

John S. Blanchard, Molecular Mechanisms of Drug Resistance in Mycobacterium Tuberculosis, Annu. Rev. Biochem., vol. 65:215-239, 1996.
Kaza Suguna et al., Structural Basis for Triclosan and NAD Binding to Enoyl-ACP Reductase of Plasmodium Falciparum, Biochemical and Biophysical Research Communication, vol. 283:224-228, 2001.
National Center for Biotechnology Information General Identifier No. 7489537, Accession No. T03735, Jun. 3, 2002, De Boer, G.J.
National Center for Biotechnology Information General Identifier No. 7489119, Accession No. T03229, Mar. 3, 2002, De Boer, G.J.
National Center for Biotechnology Information General Identifier No. 14422257, Accession No. CAC41367, Jun. 12, 2001, McDonald, F.
A.R. Slabas et. al., Induction, Purification and Characterization of NADH-Specific Enoyl Acyl Carrier Protein Reductase from Developing Seeds of Oil Seed Rape (*Brassica Napus*), Biochim. Biophys. Acta., vol. 877:271-280, 1986.
Sapan Parikh et al., Roles of Tyrosine 158 and Lysine 165 in the Catalytic Mechanism of InhA, the Enoyl-ACP Reductase from Mycobacterium tuberculosis, Biochemistry 38:13623-13634, 1999.
Zhonglin Mou et al., Deficiency in Fatty Acid Synthase Leads to Premature Cell Death and Dramatic Alterations in Plant Morphology, The Plant Cell, vol. 12:405-417, Mar. 2000.
De Boer et al., Sequence of an Oryza sativacDNA encoding enoly-ACP reductase, Database GenEMBL Accession AJ003025, Nov. 30, 1997.
Database SPTREMBL_23, EMBL Database Accession No. 024207, G. J. De Boer et al., Jan. 1, 1998, Sequence of an Oryza sativa cDNA encoding enoyl-ACP reductase.

* cited by examiner

*Primary Examiner*—Elizabeth F. McElwain

(57) ABSTRACT

This invention relates to an isolated nucleic acid fragment encoding corn (*Zea maize*) and soybean (*Glycine max*) enoyl-ACP reductase. The invention also relates to the construction of a recombinant DNA construct encoding all or a portion of the enoyl-ACP reductase, in sense or antisense orientation, wherein expression of the recombinant DNA construct results in production of altered levels of the enoyl-ACP reductase in a transformed host cell.

11 Claims, 4 Drawing Sheets

Figure 1A

```
                  *              *                 **                                *
SEQ ID NO:11      MGASAATGMQMVAARPCISASQGMLTSRAAVSRIGRALSTTTGFATCPRICYSSPL----
SEQ ID NO:12      MAASAASSFQITIARPSIFSTKRISSVCSTKFCADTRKQSWNRLASSCQVSSTQNFWRNF
SEQ ID NO:2       MTASAAAGVQMVAARPCISASPGILTARVAVSRTDCMLSTTATF---PKISCSWPL----
SEQ ID NO:4       MGASAATGMQMVAARPCISASQGMLTSRAAVSRIGRALSTTTGFATCPRICYSSPL----
SEQ ID NO:8       MATTV-SNLPTAMSRPKIPSSQRIANVGPALLGARSKVGSCYKLASVCHVASAQPFQQGL
                  1                                                           60

*              ********  **  *       ****
SEQ ID NO:11      ----GSSKRSGVAIRAMSSESGPQ---GLPIDLRGKRAFIAGVADDNGYGWAIAKALAAA
SEQ ID NO:12      TSTSQ--KLEKVVTKAKSEADGSKAASGLPIDLKGKRAFIAGIADDNGYGWAIAKSLAAA
SEQ ID NO:2       -RFKRNDVVVRAISEECGPQ---GLPIDLRGKRAFIAGVADDNGYGWAIAKALAAA
SEQ ID NO:4       ----GSSKRSGVAIRAMSSESGPQ---GLPIDLRGKRAFIAGVADDNGYGWAIAKALAAA
SEQ ID NO:8       TMTSGAVKYDKIITKAMSESSSNKEVAGLPIDLKGKRAFIAGVADDNGYGWAIAKSLAAA
                  61                                                          120

********************  ************** *  *     *     ******
SEQ ID NO:11      GAEILVGTWVPALNIFETSLRRGKFDESRKLPDGSLMEIVKVNPLDAVYDSPEDVPEDVK
SEQ ID NO:12      GAEILVGTWVPALNIFETSLRRGKFDESRKLPDGSLMEITKVYPLDAVFDSLEDVPEDIK
SEQ ID NO:2       GAEILVGTWVPALNIFETSLRRGKFDESRKLPDGSLMDIVKVYPLDAVFDSPDDVPEDVK
SEQ ID NO:4       GAEILVGTWVPALNIFETSLRRGKFDESRKLPDGSLMEIVKVYPLDAVYDSPEDVPEDVK
SEQ ID NO:8       GAEILVGTWVPALNIFESSLRRGKFDESRKLQDGSLMEIAKVYPLDAVYDSPEDVPEDVK
                  121                                                         180
```

Figure 1B

```
              ******   *** ******    ****     *     ** *** ***  *  *  **********
SEQ ID NO:11  GNKRYAGSSNWTVKEVAESVKNDFGSMDIMVHSLANGPEVTKPLLETSRRGYLAALSASS
SEQ ID NO:12  SNKRYAGSSKWTVSEAAESVKEDFGSIDILVHSLANGPEVTKPLLETTRKGYLAAISASS
SEQ ID NO: 2  SNKRYAGASNWTVKEVVESVRNDFGSIDILVHSLANGPEVTKPLLETSRRGYLAAISASS
SEQ ID NO: 4  GNKRYAGSSNWTVKEVAESVKNDFGSIDILVHSLANGPEVTKPLLETSRRGYLAALSASS
SEQ ID NO: 8  ANKRYAGATNWTVQEVAESVKKDFGTIDILVHSLANGPEVSKLLSETSRKGYLAALSASS
              181                                                        240

** *** ********** *  * **********   *****   ********** LESDTKVLAFEAGRK
SEQ ID NO:11  YSFVSLLQHFLPIMNPGGASISLTYIASERAI  PGYGGMSSAKAA  LESDTKVLAFEAGRK
SEQ ID NO:12  YSYVSLLKHFLPIMNPGGSSISLTYIASERII  PGYGGMSSAKAA  LESDTRVLAFEAGRK
SEQ ID NO: 2  YSYVSLLQHFLPIMNPGGASISLTYIASERAI  PGYGGMSSAKAA  LESDTRVLAFEAGRK
SEQ ID NO: 4  YSFVSLLQHFLPIMNPGGASISLTYIASERAI  PGYGGMSSAKAA  LESDTKVLAFEAGRK
SEQ ID NO: 8  YSYISLLKHFLPIMNPDGSAISLTYIASERII  PGYGGMSSAKAA  LESDTRVLAFEAGRK
              241                                                        300

***********   *                        *    *   ********
SEQ ID NO:11  GKIRVNTISAGPLGSRAAGPLGSRAAKAIGFIEKIIEYSYVYAPFQKELLADEVGNTAAF
SEQ ID NO:12  KKVRVNTISAGPLR------SRAAKAIGFIDMMIDYSIANAPLQKELSADEVGNTAAF
SEQ ID NO: 2  GKIRVNTISAGPLG------SRAAKAIGFIEKMIEYSYVNAPLQKELLADEVGNTAAF
SEQ ID NO: 4  GKIRVNTISAGPLG------SRAAKAIGFIEKMIEYSYVNAPLQKELLADEVGNTAAF
SEQ ID NO: 8  KRIRVNTISAGPLG------SRAAKAIGFIDMMIDYSFTNAPLQKELHAEEVGNTAAF
              301                                                        360
```

Figure 1C

```
                  ***  *********  *  ****  ** **   ***
SEQ ID NO:11      LVSPLASAITGSTVYVHNGLNTMGLAVDSP------TTSS
SEQ ID NO:12      LASPLASAITGAVIYVDNGLNAMGVGIDSPLFKELNIPKSEE
SEQ ID NO: 2      LVSSLASAITGSTVYVDNGLNTMGLAIDSP------TITS
SEQ ID NO: 4      LVSPLASAITGSTVYVDNGLNTMGLAVDSP------TISS
SEQ ID NO: 8      LSSPLASAITGAVIYVDNGLNAMGVGVDSPIFKELDIPKEHH
                  361                                    402
```

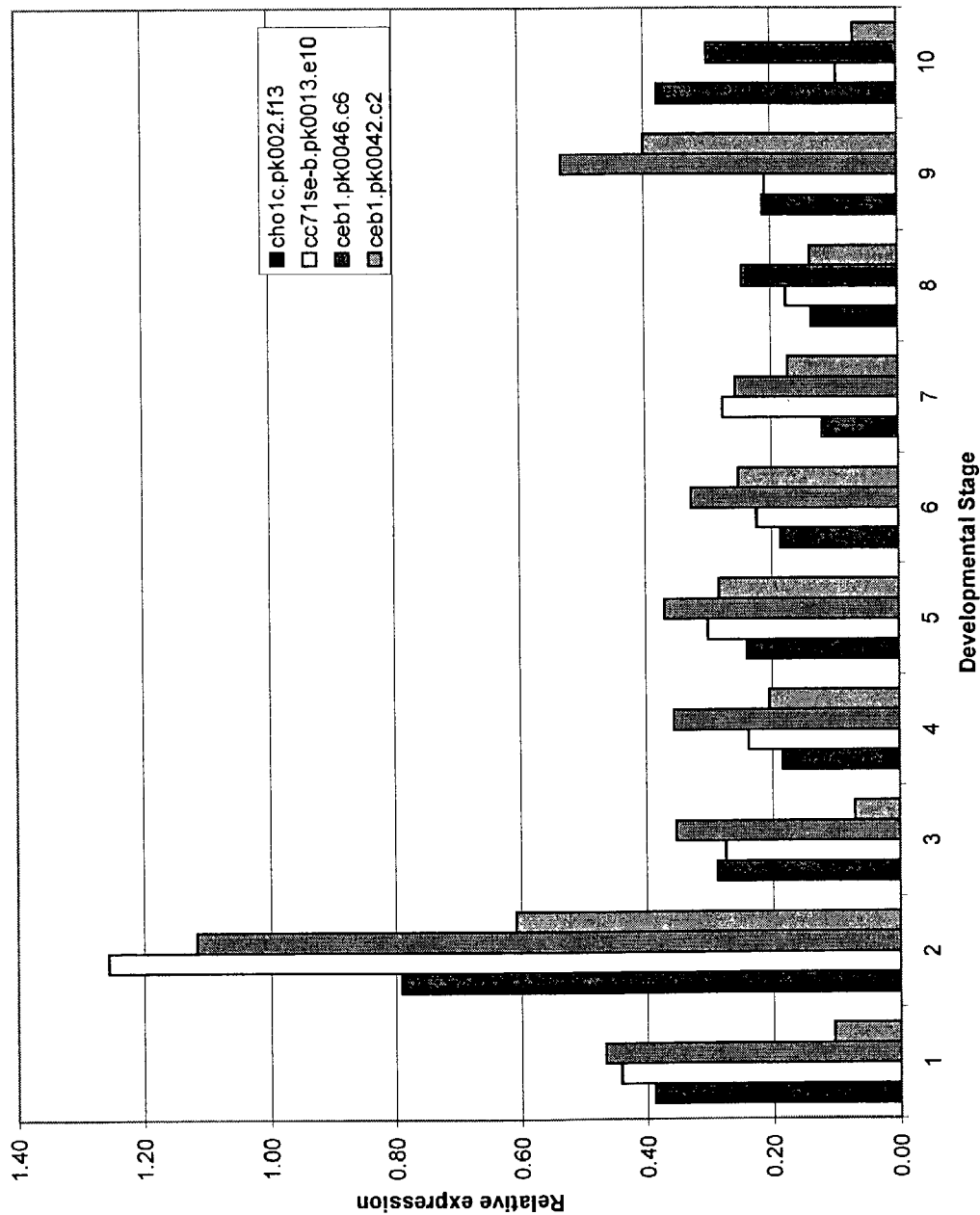

SEQUENCE LISTING

<160> NUMBER OF SEQ ID NOS: 21

<210> SEQ ID NO 1
<211> LENGTH: 1474
<212> TYPE: DNA
<213> ORGANISM: Zea mays

-continued

<400> SEQUENCE: 1

```
gctcagtcag atccccgtcc cgcatttcct aaggccagtt ggcattgaag acgatgactg      60
cttctgcagc tgctggtgtg cagatggtgg ctgcacgccc ttgcatttcg gcctcgccag     120
gaattcttac cgcacgggta gcagtttcta ggactgattg catgctcagt accactgcta     180
cattccccaa aatcagctgc tcctggcctc taaggtttaa gcgcaatgat gttgttgtaa     240
gagcaatatc ggaagagtgt ggcccgcagg ggcttcccat tgatctcaga ggtaaaaggg     300
cattcattgc tggagttgct gatgataatg gctatggatg gcaattgcg aaggcacttg      360
ctgcggctgg tgctgaaatt cttgtgggta catgggtgcc ggcacttaac atatttgaga     420
caagtctgag gcgtggaaag tttgatgaat cacggaagct gccagatgga tctcttatgg     480
atattgttaa agtctatcca cttgatgctg tctacgattc ccctgatgat gttcctgaag     540
atgtcaaatc gaacaaaaga tatgcagggg catcaaactg gacagtaaag gaagttgttg     600
aatcagtgag gaatgatttt ggcagcattg acatactagt gcattctctt gctaatggcc     660
cagaggtaac gaagcctttg ttggaaacct caagaagagg ctatcttgcg gcaatttctg     720
catccagtta ctcctatgtt tcattgcttc agcacttcct tcctataatg aatcccggtg     780
gtgctagcat ctctctaaca tacattgcat ctgaaagggc gattcctggg tatggtggtg     840
ggatgagttc tgctaaagca gctcttgaga gtgatacacg ggtgcttgca ttcgaagctg     900
ggcgaaaagg caaaatcaga gttaacacca tatcagcagg ccctcttggg agccgagctg     960
ctaaggcaat tggatttatt gagaagatga tagagtactc atatgttaat gcaccattgc    1020
agaaggagct gttggctgat gaggtgggga acacagctgc attcctggtt tcttcattgg    1080
cttctgccat caccggctcg actgtttatg ttgacaatgg gctcaataca atggggcttg    1140
caattgacag ccctaccata acgtcataga tgtggttgtg gtagatagac gaccttttcct   1200
gctgcattgc ggtatcatcc ttgaataaag atcatagtta gttattagta tgagaggtaa    1260
gggcaggaaa gggggaaaat tatgaactgg tcttttgcgc tttctttgct ggagaggaac    1320
attagagcga tttccagaat gatgggatgc tattatgtga tttcatatga ttcgaagca    1380
gtacaataac tccctagatg agctgtcata actatactta tgtttaagaa acagcctaca    1440
tcttaggtca ctaaaaaaaa aaaaaaaaaa aaaa                                1474
```

<210> SEQ ID NO 2
<211> LENGTH: 371
<212> TYPE: PRT
<213> ORGANISM: Zea mays

<400> SEQUENCE: 2

```
Met Thr Ala Ser Ala Ala Ala Gly Val Gln Met Val Ala Ala Arg Pro
 1               5                  10                  15

Cys Ile Ser Ala Ser Pro Gly Ile Leu Thr Ala Arg Val Ala Val Ser
                20                  25                  30

Arg Thr Asp Cys Met Leu Ser Thr Thr Ala Thr Phe Pro Lys Ile Ser
            35                  40                  45

Cys Ser Trp Pro Leu Arg Phe Lys Arg Asn Asp Val Val Arg Ala
        50                  55                  60

Ile Ser Glu Glu Cys Gly Pro Gln Gly Leu Pro Ile Asp Leu Arg Gly
 65                  70                  75                  80

Lys Arg Ala Phe Ile Ala Gly Val Ala Asp Asp Asn Gly Tyr Gly Trp
                85                  90                  95
```

```
Ala Ile Ala Lys Ala Leu Ala Ala Ala Gly Ala Glu Ile Leu Val Gly
            100                 105                 110

Thr Trp Val Pro Ala Leu Asn Ile Phe Glu Thr Ser Leu Arg Arg Gly
        115                 120                 125

Lys Phe Asp Glu Ser Arg Lys Leu Pro Asp Gly Ser Leu Met Asp Ile
    130                 135                 140

Val Lys Val Tyr Pro Leu Asp Ala Val Tyr Asp Ser Pro Asp Asp Val
145                 150                 155                 160

Pro Glu Asp Val Lys Ser Asn Lys Arg Tyr Ala Gly Ala Ser Asn Trp
                165                 170                 175

Thr Val Lys Glu Val Val Glu Ser Val Arg Asn Asp Phe Gly Ser Ile
            180                 185                 190

Asp Ile Leu Val His Ser Leu Ala Asn Gly Pro Glu Val Thr Lys Pro
        195                 200                 205

Leu Leu Glu Thr Ser Arg Arg Gly Tyr Leu Ala Ala Ile Ser Ala Ser
    210                 215                 220

Ser Tyr Ser Tyr Val Ser Leu Leu Gln His Phe Leu Pro Ile Met Asn
225                 230                 235                 240

Pro Gly Gly Ala Ser Ile Ser Leu Thr Tyr Ile Ala Ser Glu Arg Ala
                245                 250                 255

Ile Pro Gly Tyr Gly Gly Met Ser Ser Ala Lys Ala Ala Leu Glu
            260                 265                 270

Ser Asp Thr Arg Val Leu Ala Phe Glu Ala Gly Arg Lys Gly Lys Ile
    275                 280                 285

Arg Val Asn Thr Ile Ser Ala Gly Pro Leu Gly Ser Arg Ala Ala Lys
290                 295                 300

Ala Ile Gly Phe Ile Glu Lys Met Ile Glu Tyr Ser Tyr Val Asn Ala
305                 310                 315                 320

Pro Leu Gln Lys Glu Leu Leu Ala Asp Glu Val Gly Asn Thr Ala Ala
                325                 330                 335

Phe Leu Val Ser Ser Leu Ala Ser Ala Ile Thr Gly Ser Thr Val Tyr
            340                 345                 350

Val Asp Asn Gly Leu Asn Thr Met Gly Leu Ala Ile Asp Ser Pro Thr
    355                 360                 365

Ile Thr Ser
    370

<210> SEQ ID NO 3
<211> LENGTH: 1635
<212> TYPE: DNA
<213> ORGANISM: Oryza sativa

<400> SEQUENCE: 3
gcacgagcgc ggagtcgcca acacgaaccc ccctcctctc ttcctccctc cctcggtctc      60
atcgaaaacc cccactatta ctaccactcc ccctcgcctt ctccgcctcc acagcgacca     120
gcagccgcgc cgagctccca gatccctcgt gcattccacc ttctcccgag gacgatgggc     180
gcttctgcag ctaccggtat gcagatggtg gctgcacgcc cctgcatctc agcctcccag     240
ggaatgctta cttccagggc ggcggtctcc cggattggcc gcgcactcag caccaccact     300
ggctttgcaa cctgtcccag aatctgctac tccagccctc ttggttcttc aagcgcagc     360
ggtgtcgcca tcagagcaat gtcaagcgaa gtggccccc aaggcctacc aattgatctt     420
agaggtaaaa gggcgttcat tgctggagtt gctgatgaca atggctatgg ctgggcaatt     480
gcaaaggctc ttgctgctgc tggtgctgaa attcttgttg gtacatgggt gcctgcacta     540
```

```
aacatatttg agacaagcct aaggcgtgga agtttgatg aatcacgaaa gctgcctgat      600
ggatctctta tggaaattgt taaagtctat ccacttgatg ctgtctatga ttcccctgaa      660
gatgttcctg aagatgtcaa aggaaacaaa aggtatgctg ggtcatcaaa ttggactgtt      720
aaggaagttg ctgagtcagt caagaatgac tttggcagca ttgacatttt ggtgcattct      780
ctagctaatg gtccagaggt aacaaaacca ctattggaga catcaagaag agggtatctt      840
gctgcactgt cagcatcgag ttactccttc gtctctttgc ttcagcactt ccttcctata      900
atgaatccag gtggtgcttc catctctcta acatacattg catctgaaag ggcaattcct      960
ggatatggtg gtggcatgag ttcagctaaa gcagctcttg agagtgacac aaaagtactt     1020
gcttttgaag ctggaaggaa agggaaaatc agagttaaca ccatatctgc aggtcctttg     1080
ggaagccgag ctgccaaggc aattggattc attgagaaga tgatagaata ctcttatgtt     1140
aatgcaccgt tgcagaaaga actgttggca gacgaagtgg ggaacacagc agcattcctg     1200
gtgtctccat tggcttccgc tatcactggc tcgactgttt acgttgacaa tggactcaat     1260
acaatggggc ttgcagttga cagccctaca atatcatcat ggtgtggta tggtagatag      1320 atgggttttc ctgcttcatt gcggcttgtt tcttgaataa agagcttagt taggtagtat     1380
aagagctaag ggcaggaaga aaaaatagag catgaatcca atttggtcct tgacatttga     1440
gtaattcctg cactggggta ctcgagcaat actactaggt ggttcggaat gattcaagcc     1500
ccagttacca atgttctgtg ctgtatcttg aaattttaa tcattgatac tgtgtttctt      1560
cgaaaaaaaa aaaaaaaaaa aaaaaaaaaa aaaaaaaaaa aaaaaaaaaa aaaaaaaaaa     1620
aaaaaaaaaa aaaaa                                                     1635
```

<210> SEQ ID NO 4
<211> LENGTH: 375
<212> TYPE: PRT
<213> ORGANISM: Oryza sativa

<400> SEQUENCE: 4

```
Met Gly Ala Ser Ala Ala Thr Gly Met Gln Met Val Ala Ala Arg Pro
  1               5                  10                  15

Cys Ile Ser Ala Ser Gln Gly Met Leu Thr Ser Arg Ala Ala Val Ser
                 20                  25                  30

Arg Ile Gly Arg Ala Leu Ser Thr Thr Thr Gly Phe Ala Thr Cys Pro
             35                  40                  45

Arg Ile Cys Tyr Ser Ser Pro Leu Gly Ser Ser Lys Arg Ser Gly Val
         50                  55                  60

Ala Ile Arg Ala Met Ser Ser Glu Ser Gly Pro Gln Gly Leu Pro Ile
 65                  70                  75                  80

Asp Leu Arg Gly Lys Arg Ala Phe Ile Ala Gly Val Ala Asp Asp Asn
                 85                  90                  95

Gly Tyr Gly Trp Ala Ile Ala Lys Ala Leu Ala Ala Gly Ala Glu
            100                 105                 110

Ile Leu Val Gly Thr Trp Val Pro Ala Leu Asn Ile Phe Glu Thr Ser
            115                 120                 125

Leu Arg Arg Gly Lys Phe Asp Glu Ser Arg Lys Leu Pro Asp Gly Ser
        130                 135                 140

Leu Met Glu Ile Val Lys Val Tyr Pro Leu Asp Ala Val Tyr Asp Ser
145                 150                 155                 160

Pro Glu Asp Val Pro Glu Asp Val Lys Gly Asn Lys Arg Tyr Ala Gly
                165                 170                 175
```

```
Ser Ser Asn Trp Thr Val Lys Glu Val Ala Glu Ser Val Lys Asn Asp
            180                 185                 190

Phe Gly Ser Ile Asp Ile Leu Val His Ser Leu Ala Asn Gly Pro Glu
        195                 200                 205

Val Thr Lys Pro Leu Leu Glu Thr Ser Arg Arg Gly Tyr Leu Ala Ala
    210                 215                 220

Leu Ser Ala Ser Ser Tyr Ser Phe Val Ser Leu Leu Gln His Phe Leu
225                 230                 235                 240

Pro Ile Met Asn Pro Gly Gly Ala Ser Ile Ser Leu Thr Tyr Ile Ala
                245                 250                 255

Ser Glu Arg Ala Ile Pro Gly Tyr Gly Gly Met Ser Ser Ala Lys
                260                 265                 270

Ala Ala Leu Glu Ser Asp Thr Lys Val Leu Ala Phe Glu Ala Gly Arg
            275                 280                 285

Lys Gly Lys Ile Arg Val Asn Thr Ile Ser Ala Gly Pro Leu Gly Ser
    290                 295                 300

Arg Ala Ala Lys Ala Ile Gly Phe Ile Glu Lys Met Ile Glu Tyr Ser
305                 310                 315                 320

Tyr Val Asn Ala Pro Leu Gln Lys Glu Leu Leu Ala Asp Glu Val Gly
                325                 330                 335

Asn Thr Ala Ala Phe Leu Val Ser Pro Leu Ala Ser Ala Ile Thr Gly
            340                 345                 350

Ser Thr Val Tyr Val Asp Asn Gly Leu Asn Thr Met Gly Leu Ala Val
        355                 360                 365

Asp Ser Pro Thr Ile Ser Ser
370                 375

<210> SEQ ID NO 5
<211> LENGTH: 513
<212> TYPE: DNA
<213> ORGANISM: Oryza sativa
<220> FEATURE:
<221> NAME/KEY: unsure
<222> LOCATION: (243)
<223> OTHER INFORMATION: n = A, C, G or T
<220> FEATURE:
<221> NAME/KEY: unsure
<222> LOCATION: (260)
<223> OTHER INFORMATION: n = A, C, G or T
<220> FEATURE:
<221> NAME/KEY: unsure
<222> LOCATION: (266)
<223> OTHER INFORMATION: n = A, C, G or T
<220> FEATURE:
<221> NAME/KEY: unsure
<222> LOCATION: (272)
<223> OTHER INFORMATION: n = A, C, G or T
<220> FEATURE:
<221> NAME/KEY: unsure
<222> LOCATION: (275)
<223> OTHER INFORMATION: n = A, C, G or T
<220> FEATURE:
<221> NAME/KEY: unsure
<222> LOCATION: (294)
<223> OTHER INFORMATION: n = A, C, G or T
<220> FEATURE:
<221> NAME/KEY: unsure
<222> LOCATION: (327)
<223> OTHER INFORMATION: n = A, C, G or T
<220> FEATURE:
<221> NAME/KEY: unsure
<222> LOCATION: (333)
<223> OTHER INFORMATION: n = A, C, G or T
<220> FEATURE:
<221> NAME/KEY: unsure
```

```
<222> LOCATION: (340)
<223> OTHER INFORMATION: n = A, C, G or T
<220> FEATURE:
<221> NAME/KEY: unsure
<222> LOCATION: (348)
<223> OTHER INFORMATION: n = A, C, G or T
<220> FEATURE:
<221> NAME/KEY: unsure
<222> LOCATION: (366)
<223> OTHER INFORMATION: n = A, C, G or T
<220> FEATURE:
<221> NAME/KEY: unsure
<222> LOCATION: (373)
<223> OTHER INFORMATION: n = A, C, G or T
<220> FEATURE:
<221> NAME/KEY: unsure
<222> LOCATION: (403)
<223> OTHER INFORMATION: n = A, C, G or T
<220> FEATURE:
<221> NAME/KEY: unsure
<222> LOCATION: (418)
<223> OTHER INFORMATION: n = A, C, G or T
<220> FEATURE:
<221> NAME/KEY: unsure
<222> LOCATION: (420)
<223> OTHER INFORMATION: n = A, C, G or T
<220> FEATURE:
<221> NAME/KEY: unsure
<222> LOCATION: (439)
<223> OTHER INFORMATION: n = A, C, G or T
<220> FEATURE:
<221> NAME/KEY: unsure
<222> LOCATION: (442)..(443)
<223> OTHER INFORMATION: n = A, C, G or T
<220> FEATURE:
<221> NAME/KEY: unsure
<222> LOCATION: (461)
<223> OTHER INFORMATION: n = A, C, G or T
<220> FEATURE:
<221> NAME/KEY: unsure
<222> LOCATION: (467)
<223> OTHER INFORMATION: n = A, C, G or T
<220> FEATURE:
<221> NAME/KEY: unsure
<222> LOCATION: (483)
<223> OTHER INFORMATION: n = A, C, G or T
<220> FEATURE:
<221> NAME/KEY: unsure
<222> LOCATION: (485)
<223> OTHER INFORMATION: n = A, C, G or T
<220> FEATURE:
<221> NAME/KEY: unsure
<222> LOCATION: (493)
<223> OTHER INFORMATION: n = A, C, G or T
<220> FEATURE:
<221> NAME/KEY: unsure
<222> LOCATION: (501)
<223> OTHER INFORMATION: n = A, C, G or T

<400> SEQUENCE: 5
gccatgtccg ccatgcgcag cctgatgcaa aagcccaacg gcgcactgcg cagccaagag      60
gctggcgcgc cctgctgcca gccgcgccat gagcgtcaag gtgcaggcct cgaacctggc     120
cgtggacctg cgcggcaaga aagcgttcgt ggccggcgtg gctgatgacc aaggcttcgg     180
ctgggccatc tccaagtgcc tggcggaggc tggcgcccaa gtgtctcttg ggcgtctggg     240
tgncccgcgc tgaaaaatcn tcctanacca anttncaagg cgtggggaag tttngaccca     300
agccgcaaag ctttccaaac gggaaanatg atnggagttn aaagcaanaa tctaccccca     360
atgggncggc cgnccttttta caacccttttg ttaacgtgcc ccnaagggag aattggcnan     420
caaaaaaaaa cggcttaanc cnnggggaaa actcccgggt ngggaanccg ttttccaaa     480 ggngnggccc canaaaaggg nccccaaaag gga                                  513
```

<210> SEQ ID NO 6
<211> LENGTH: 69
<212> TYPE: PRT
<213> ORGANISM: Oryza sativa

<400> SEQUENCE: 6

```
Cys Lys Ser Pro Thr Ala His Cys Ala Ala Lys Arg Leu Ala Arg Pro
  1               5                  10                  15
Ala Ala Ser Arg Ala Met Ser Val Lys Val Gln Ala Ser Asn Leu Ala
                 20                  25                  30
Val Asp Leu Arg Gly Lys Lys Ala Phe Val Ala Gly Val Ala Asp Asp
             35                  40                  45
Gln Gly Phe Gly Trp Ala Ile Ser Lys Cys Leu Ala Glu Ala Gly Ala
         50                  55                  60
Gln Val Ser Leu Gly
 65
```

<210> SEQ ID NO 7
<211> LENGTH: 1431
<212> TYPE: DNA
<213> ORGANISM: Glycine max

<400> SEQUENCE: 7

```
gcacgagctt acaactctct ctcgtttctc tctccagatc taggttctct gcatcatttt      60
tcatttggac aagatggcaa caacagtttc caacttgcca actgctatgt caagacccaa     120
gattccttca tcacaaagga ttgcaaatgt aggtcctgca cttcttggag ccagatctaa     180
ggttggttca tgttataaac tggcaagtgt ttgtcatgtt gcgtcagcac aacctttcca     240
gcaggggttg acaatgacat caggtgctgt aaaatatgac aaaatcataa caaaggcaat     300
gtccgagtct agttcaaaca aggaagttgc aggattgcca attgatttga aggtaaaag      360
ggctttcatt gctggtgtgg ctgatgacaa tggatatggc tgggcaatag caaaatctct     420
tgcagcagca ggagctgaaa ttcttgtcgg cacatgggta cctgctttaa atatatttga     480
gtccagtcta cgacgtggaa aatttgacga gtcacgcaaa ttacaagatg gttcattgat     540
ggagattgct aaagtgtatc ctttggatgc agtatatgac agtcctgaag atgtcccgga     600
agatgtgaaa gctaacaagc gctatgctgg agccacaaat tggactgtac aggaagttgc     660
tgaatctgtc aagaaggatt ttggcactat cgacatactt gtgcactcgc ttgctaatgg     720
accagaggtc agcaaactat tgtccgagac atctcggaaa ggatatcttg ctgccctgtc     780
tgcatcaagt tactcttata tttctttact caaacacttt cttccaatca tgaacccaga     840
tggatctgca atttctctta catacattgc ttcagaaagg atcattcctg atatggtgg      900
tggtatgagt tctgcaaaag ctgctttaga aagtgataca agagtgcttg cttttgaagc     960
tggtagaaag aaaagaatca gagtcaatac tatatctgca ggtccattgg gaagccgtgc    1020
agcaaaagca attggcttca ttgacatgat gattgactat tcgtttacca atgcaccact    1080
gcagaaagaa ctacatgctg aggaggttgg caacactgct gctttcttgt catcaccctt    1140
ggcatcagct atcacaggtg ctgttatata tgttgacaat ggtctaaacg ccatgggggt    1200
tggagttgac agtccaatat ttaaagaact tgacattcca aaagagcatc attgaagtgc    1260
atagtatatc tctacaccaa ctaaagattt atacggccta gtatgatgaa aaaaagctga    1320
ggaagttagt ttttgcaatt tcataaatta gtaaacggtt gtttgaactt tgctaccatt    1380
gattttcatt aattactatc cacttttcat tatcctctaa aaaaaaaaa a              1431
```

<210> SEQ ID NO 8
<211> LENGTH: 393
<212> TYPE: PRT
<213> ORGANISM: Glycine max

<400> SEQUENCE: 8

```
Met Ala Thr Thr Val Ser Asn Leu Pro Thr Ala Met Ser Arg Pro Lys
  1               5                  10                  15

Ile Pro Ser Ser Gln Arg Ile Ala Asn Val Gly Pro Ala Leu Leu Gly
                 20                  25                  30

Ala Arg Ser Lys Val Gly Ser Cys Tyr Lys Leu Ala Ser Val Cys His
             35                  40                  45

Val Ala Ser Ala Gln Pro Phe Gln Gln Gly Leu Thr Met Thr Ser Gly
         50                  55                  60

Ala Val Lys Tyr Asp Lys Ile Ile Thr Lys Ala Met Ser Glu Ser Ser
 65                  70                  75                  80

Ser Asn Lys Glu Val Ala Gly Leu Pro Ile Asp Leu Lys Gly Lys Arg
                 85                  90                  95

Ala Phe Ile Ala Gly Val Ala Asp Asp Asn Gly Tyr Gly Trp Ala Ile
            100                 105                 110

Ala Lys Ser Leu Ala Ala Gly Ala Glu Ile Leu Val Gly Thr Trp
            115                 120                 125

Val Pro Ala Leu Asn Ile Phe Glu Ser Ser Leu Arg Arg Gly Lys Phe
        130                 135                 140

Asp Glu Ser Arg Lys Leu Gln Asp Gly Ser Leu Met Glu Ile Ala Lys
145                 150                 155                 160

Val Tyr Pro Leu Asp Ala Val Tyr Asp Ser Pro Glu Asp Val Pro Glu
                165                 170                 175

Asp Val Lys Ala Asn Lys Arg Tyr Ala Gly Ala Thr Asn Trp Thr Val
            180                 185                 190

Gln Glu Val Ala Glu Ser Val Lys Lys Asp Phe Gly Thr Ile Asp Ile
        195                 200                 205

Leu Val His Ser Leu Ala Asn Gly Pro Glu Val Ser Lys Leu Leu Ser
    210                 215                 220

Glu Thr Ser Arg Lys Gly Tyr Leu Ala Ala Leu Ser Ala Ser Ser Tyr
225                 230                 235                 240

Ser Tyr Ile Ser Leu Leu Lys His Phe Leu Pro Ile Met Asn Pro Asp
                245                 250                 255

Gly Ser Ala Ile Ser Leu Thr Tyr Ile Ala Ser Glu Arg Ile Ile Pro
            260                 265                 270

Gly Tyr Gly Gly Gly Met Ser Ala Lys Ala Ala Leu Glu Ser Asp
        275                 280                 285

Thr Arg Val Leu Ala Phe Glu Ala Gly Arg Lys Lys Arg Ile Arg Val
290                 295                 300

Asn Thr Ile Ser Ala Gly Pro Leu Gly Ser Arg Ala Ala Lys Ala Ile
305                 310                 315                 320

Gly Phe Ile Asp Met Met Ile Asp Tyr Ser Phe Thr Asn Ala Pro Leu
                325                 330                 335

Gln Lys Glu Leu His Ala Glu Val Gly Asn Thr Ala Ala Phe Leu
            340                 345                 350

Ser Ser Pro Leu Ala Ser Ala Ile Thr Gly Ala Val Ile Tyr Val Asp
        355                 360                 365

Asn Gly Leu Asn Ala Met Gly Val Gly Val Asp Ser Pro Ile Phe Lys
    370                 375                 380
```

Glu Leu Asp Ile Pro Lys Glu His His
385                 390

<210> SEQ ID NO 9
<211> LENGTH: 531
<212> TYPE: DNA
<213> ORGANISM: Triticum aestivum
<220> FEATURE:
<221> NAME/KEY: unsure
<222> LOCATION: (189)
<223> OTHER INFORMATION: n = A, C, G or T
<220> FEATURE:
<221> NAME/KEY: unsure
<222> LOCATION: (334)
<223> OTHER INFORMATION: n = A, C, G or T
<220> FEATURE:
<221> NAME/KEY: unsure
<222> LOCATION: (384)
<223> OTHER INFORMATION: n = A, C, G or T
<220> FEATURE:
<221> NAME/KEY: unsure
<222> LOCATION: (393)
<223> OTHER INFORMATION: n = A, C, G or T
<220> FEATURE:
<221> NAME/KEY: unsure
<222> LOCATION: (400)
<223> OTHER INFORMATION: n = A, C, G or T
<220> FEATURE:
<221> NAME/KEY: unsure
<222> LOCATION: (408)
<223> OTHER INFORMATION: n = A, C, G or T
<220> FEATURE:
<221> NAME/KEY: unsure
<222> LOCATION: (432)
<223> OTHER INFORMATION: n = A, C, G or T
<220> FEATURE:
<221> NAME/KEY: unsure
<222> LOCATION: (448)
<223> OTHER INFORMATION: n = A, C, G or T
<220> FEATURE:
<221> NAME/KEY: unsure
<222> LOCATION: (483)
<223> OTHER INFORMATION: n = A, C, G or T
<220> FEATURE:
<221> NAME/KEY: unsure
<222> LOCATION: (496)..(497)
<223> OTHER INFORMATION: n = A, C, G or T
<220> FEATURE:
<221> NAME/KEY: unsure
<222> LOCATION: (503)
<223> OTHER INFORMATION: n = A, C, G or T
<220> FEATURE:
<221> NAME/KEY: unsure
<222> LOCATION: (521)..(522)
<223> OTHER INFORMATION: n = A, C, G or T
<220> FEATURE:
<221> NAME/KEY: unsure
<222> LOCATION: (529)
<223> OTHER INFORMATION: n = A, C, G or T

<400> SEQUENCE: 9
ggatctctta tggatattgt taaagtctat ccacttgatg ctgtctacga ttcccctgat    60
gatgttcctg aagatgtcaa atcgaacaaa agatatgcag ggcatcaaa ctggacagta   120 aaggaagttg ttgaatcagt gaggaatgat tttggcagca ttgacatact aagtgcattc   180
tcttgctant ggcccagagg taacgaagcc tttgttggga aacctcaaga agaggctatc   240
ttgcggcaat ttctgcatcc agttactcct atgtttcatt gcttcagcac ttccttccca   300
ataatgatcc cggttggtgc tagcatctcc tctnacatac attgcatcct gaaaagggcg   360
attcccgggt atgtggtgga atangttttg gcnaaaagcan ctcttganaa tgatacacgg   420
tgcttgcatt cnaagcttgg cgaaaagnaa atcagagtta cacatatcag cagcctcttg   480
gancccactg ctaagnnatt ggnttatgag aaaatattga nnccaaatnt t          531

<210> SEQ ID NO 10
<211> LENGTH: 158
<212> TYPE: PRT
<213> ORGANISM: Triticum aestivum
<220> FEATURE:
<221> NAME/KEY: UNSURE
<222> LOCATION: (63)
<223> OTHER INFORMATION: Xaa = ANY AMINO ACID
<220> FEATURE:
<221> NAME/KEY: UNSURE
<222> LOCATION: (112)
<223> OTHER INFORMATION: Xaa = ANY AMINO ACID
<220> FEATURE:
<221> NAME/KEY: UNSURE
<222> LOCATION: (128)
<223> OTHER INFORMATION: Xaa = ANY AMINO ACID
<220> FEATURE:
<221> NAME/KEY: UNSURE
<222> LOCATION: (134)
<223> OTHER INFORMATION: Xaa = ANY AMINO ACID
<220> FEATURE:
<221> NAME/KEY: UNSURE
<222> LOCATION: (136)
<223> OTHER INFORMATION: Xaa = ANY AMINO ACID
<220> FEATURE:
<221> NAME/KEY: UNSURE
<222> LOCATION: (150)
<223> OTHER INFORMATION: Xaa = ANY AMINO ACID

<400> SEQUENCE: 10

Gly Ser Leu Met Asp Ile Val Lys Val Tyr Pro Leu Asp Ala Val Tyr
 1               5                  10                  15

Asp Ser Pro Asp Val Pro Glu Asp Val Lys Ser Asn Lys Arg Tyr
             20                  25                  30

Ala Gly Ala Ser Asn Trp Thr Val Lys Glu Val Val Glu Ser Val Arg
         35                  40                  45

Asn Asp Phe Gly Ser Ile Asp Ile Leu Ser Ala Phe Ser Cys Xaa Trp
     50                  55                  60

Pro Arg Gly Asn Glu Ala Phe Val Gly Lys Pro Gln Glu Glu Ala Ile
 65                  70                  75                  80

Leu Arg Gln Phe Leu His Pro Val Thr Pro Met Phe His Cys Phe Ser
                 85                  90                  95

Thr Ser Phe Pro Ile Met Ile Pro Val Gly Ala Ser Ile Ser Ser Xaa
            100                 105                 110

Ile His Cys Ile Leu Lys Arg Ala Ile Pro Gly Tyr Val Val Glu Xaa
        115                 120                 125

Val Leu Ala Lys Ala Xaa Leu Xaa Asn Asp Thr Arg Cys Leu His Ser
    130                 135                 140

Lys Leu Gly Glu Lys Xaa Ile Arg Val Thr His Ile Ser Ser
145                 150                 155

<210> SEQ ID NO 11
<211> LENGTH: 383
<212> TYPE: PRT
<213> ORGANISM: Oryza sativa

<400> SEQUENCE: 11

Met Gly Ala Ser Ala Ala Thr Gly Met Gln Met Val Ala Ala Arg Pro
 1               5                  10                  15

Cys Ile Ser Ala Ser Gln Gly Met Leu Thr Ser Arg Ala Ala Val Ser
             20                  25                  30

```
Arg Ile Gly Arg Ala Leu Ser Thr Thr Gly Phe Ala Thr Cys Pro
        35                  40                  45

Arg Ile Cys Tyr Ser Ser Pro Leu Gly Ser Ser Lys Arg Ser Gly Val
 50                  55                  60

Ala Ile Arg Ala Met Ser Ser Glu Ser Gly Pro Gln Gly Leu Pro Ile
 65                  70                  75                  80

Asp Leu Arg Gly Lys Arg Ala Phe Ile Ala Gly Val Ala Asp Asp Asn
                 85                  90                  95

Gly Tyr Gly Trp Ala Ile Ala Lys Ala Leu Ala Ala Gly Ala Glu
                100                 105                 110

Ile Leu Val Gly Thr Trp Val Pro Ala Leu Asn Ile Phe Glu Thr Ser
        115                 120                 125

Leu Arg Arg Gly Lys Phe Asp Glu Ser Arg Lys Leu Pro Asp Gly Ser
    130                 135                 140

Leu Met Glu Ile Val Lys Val Asn Pro Leu Asp Ala Val Tyr Asp Ser
145                 150                 155                 160

Pro Glu Asp Val Pro Glu Asp Val Lys Gly Asn Lys Arg Tyr Ala Gly
                165                 170                 175

Ser Ser Asn Trp Thr Val Lys Glu Val Ala Glu Ser Val Lys Asn Asp
            180                 185                 190

Phe Gly Ser Met Asp Ile Met Val His Ser Leu Ala Asn Gly Pro Glu
            195                 200                 205

Val Thr Lys Pro Leu Leu Glu Thr Ser Arg Arg Gly Tyr Leu Ala Ala
        210                 215                 220

Leu Ser Ala Ser Ser Tyr Ser Phe Val Ser Leu Leu Gln His Phe Leu
225                 230                 235                 240

Pro Ile Met Asn Pro Gly Gly Ala Ser Ile Ser Leu Thr Tyr Ile Ala
                245                 250                 255

Ser Glu Arg Ala Ile Pro Gly Tyr Gly Gly Met Ser Ser Ala Lys
                260                 265                 270

Ala Ala Leu Glu Ser Asp Thr Lys Val Leu Ala Phe Glu Ala Gly Arg
        275                 280                 285

Lys Gly Lys Ile Arg Val Asn Thr Ile Ser Ala Gly Pro Leu Gly Ser
    290                 295                 300

Arg Ala Ala Gly Pro Leu Gly Ser Arg Ala Ala Lys Ala Ile Gly Phe
305                 310                 315                 320

Ile Glu Lys Ile Ile Glu Tyr Ser Tyr Val Tyr Ala Pro Phe Gln Lys
                325                 330                 335

Glu Leu Leu Ala Asp Glu Val Gly Asn Thr Ala Ala Phe Leu Val Ser
            340                 345                 350

Pro Leu Ala Ser Ala Ile Thr Gly Ser Thr Val Tyr Val His Asn Gly
        355                 360                 365

Leu Asn Thr Met Gly Leu Ala Val Asp Ser Pro Thr Thr Ser Ser
    370                 375                 380

<210> SEQ ID NO 12
<211> LENGTH: 392
<212> TYPE: PRT
<213> ORGANISM: Nicotiana tabacum

<400> SEQUENCE: 12

Met Ala Ala Ser Ala Ala Ser Ser Phe Gln Ile Thr Ile Ala Arg Pro
 1               5                  10                  15

Ser Ile Phe Ser Thr Lys Arg Ile Ser Ser Val Cys Ser Thr Lys Phe
                20                  25                  30
```

```
Cys Ala Asp Thr Arg Lys Gln Ser Trp Asn Arg Leu Ala Ser Ser Cys
            35                  40                  45

Gln Val Ser Ser Thr Gln Asn Phe Trp Arg Asn Phe Thr Ser Thr Ser
 50                  55                  60

Gln Lys Leu Glu Lys Val Val Thr Lys Ala Lys Ser Glu Ala Asp Gly
 65                  70                  75                  80

Ser Lys Ala Ala Ser Gly Leu Pro Ile Asp Leu Lys Gly Lys Arg Ala
                 85                  90                  95

Phe Ile Ala Gly Ile Ala Asp Asp Asn Gly Tyr Gly Trp Ala Ile Ala
                100                 105                 110

Lys Ser Leu Ala Ala Ala Gly Ala Glu Ile Leu Val Gly Thr Trp Val
            115                 120                 125

Pro Ala Leu Asn Ile Phe Glu Thr Ser Leu Arg Arg Gly Lys Phe Asp
        130                 135                 140

Glu Ser Arg Val Leu Pro Asp Gly Ser Leu Met Glu Ile Thr Lys Val
145                 150                 155                 160

Tyr Pro Leu Asp Ala Val Phe Asp Ser Leu Glu Asp Val Pro Glu Asp
                165                 170                 175

Ile Lys Ser Asn Lys Arg Tyr Ala Gly Ser Ser Lys Trp Thr Val Ser
                180                 185                 190

Glu Ala Ala Glu Ser Val Lys Glu Asp Phe Gly Ser Ile Asp Ile Leu
            195                 200                 205

Val His Ser Leu Ala Asn Gly Pro Glu Val Thr Lys Pro Leu Leu Glu
        210                 215                 220

Thr Thr Arg Lys Gly Tyr Leu Ala Ala Ile Ser Ala Ser Ser Tyr Ser
225                 230                 235                 240

Tyr Val Ser Leu Leu Lys His Phe Leu Pro Ile Met Asn Pro Gly Gly
                245                 250                 255

Ser Ser Ile Ser Leu Thr Tyr Ile Ala Ser Glu Arg Ile Ile Pro Gly
                260                 265                 270

Tyr Gly Gly Gly Met Ser Ser Ala Lys Ala Ala Leu Glu Ser Asp Thr
            275                 280                 285

Arg Val Leu Ala Phe Glu Ala Gly Arg Lys Lys Val Arg Val Asn
        290                 295                 300

Thr Ile Ser Ala Gly Pro Leu Arg Ser Arg Ala Ala Lys Ala Ile Gly
305                 310                 315                 320

Phe Ile Asp Met Met Ile Asp Tyr Ser Ile Ala Asn Ala Pro Leu Gln
                325                 330                 335

Lys Glu Leu Ser Ala Asp Glu Val Gly Asn Thr Ala Ala Phe Leu Ala
            340                 345                 350

Ser Pro Leu Ala Ser Ala Ile Thr Gly Ala Val Ile Tyr Val Asp Asn
        355                 360                 365

Gly Leu Asn Ala Met Gly Val Gly Ile Asp Ser Pro Leu Phe Lys Glu
    370                 375                 380

Leu Asn Ile Pro Lys Ser Glu Glu
385                 390

<210> SEQ ID NO 13
<211> LENGTH: 543
<212> TYPE: DNA
<213> ORGANISM: Zea mays
<220> FEATURE:
<221> NAME/KEY: unsure
<222> LOCATION: (427)
<223> OTHER INFORMATION: n = A, C, G or T
```

-continued

<400> SEQUENCE: 13

```
gtgggatgag ttctgctaaa gcagctcttg agagtgatac acgggtgctt gcattcgaag    60
ctgggcgaaa aggcaaaatc agagttaaca ccatatcagc aggccctctt gggagccgag   120
ctgctaaggc aattggattt attgagaaga tgatagagta ctcatatgtt aatgcaccat   180
tgcagaagga gctgttggct gatgaggtgg ggaacacagc tgcattcctg gtttcttcat   240
tggcttctgc catcaccggc tcgactgttt atgttgacaa tgggctcaat acaatggggc   300
ttgcaattga cagccctacc ataacgtcat agatgtggtt gtggtagata gacgactttc   360
ctgctgcatt cggtatcatc cttgaataaa gtcatagtta gttataaata tgagaggaag   420
ggcaggnaag ggggaaatta tgaactggct tttgcgcttt ctttgctgga gaggacatta   480
gacgtttcca gaatatggat catatgtatt caatgtcaga cagtcatact cctagatggt   540
gca                                                                543
```

<210> SEQ ID NO 14
<211> LENGTH: 109
<212> TYPE: PRT
<213> ORGANISM: Zea mays

<400> SEQUENCE: 14

```
Gly Met Ser Ser Ala Lys Ala Ala Leu Glu Ser Asp Thr Arg Val Leu
  1               5                  10                  15
Ala Phe Glu Ala Gly Arg Lys Gly Lys Ile Arg Val Asn Thr Ile Ser
             20                  25                  30
Ala Gly Pro Leu Gly Ser Arg Ala Ala Lys Ala Ile Gly Phe Ile Glu
         35                  40                  45
Lys Met Ile Glu Tyr Ser Tyr Val Asn Ala Pro Leu Gln Lys Glu Leu
     50                  55                  60
Leu Ala Asp Glu Val Gly Asn Thr Ala Ala Phe Leu Val Ser Ser Leu
 65                  70                  75                  80
Ala Ser Ala Ile Thr Gly Ser Thr Val Tyr Val Asp Asn Gly Leu Asn
                 85                  90                  95
Thr Met Gly Leu Ala Ile Asp Ser Pro Thr Ile Thr Ser
            100                 105
```

<210> SEQ ID NO 15
<211> LENGTH: 423
<212> TYPE: DNA
<213> ORGANISM: Zea mays
<220> FEATURE:
<221> NAME/KEY: unsure
<222> LOCATION: (270)
<223> OTHER INFORMATION: n = A, C, G or T
<220> FEATURE:
<221> NAME/KEY: unsure
<222> LOCATION: (352)
<223> OTHER INFORMATION: n = A, C, G or T
<220> FEATURE:
<221> NAME/KEY: unsure
<222> LOCATION: (366)
<223> OTHER INFORMATION: n = A, C, G or T
<220> FEATURE:
<221> NAME/KEY: unsure
<222> LOCATION: (376)
<223> OTHER INFORMATION: n = A, C, G or T
<220> FEATURE:
<221> NAME/KEY: unsure
<222> LOCATION: (401)
<223> OTHER INFORMATION: n = A, C, G or T
<220> FEATURE:
<221> NAME/KEY: unsure

```
<222> LOCATION: (404)
<223> OTHER INFORMATION: n = A, C, G or T
<220> FEATURE:
<221> NAME/KEY: unsure
<222> LOCATION: (412)
<223> OTHER INFORMATION: n = A, C, G or T
<220> FEATURE:
<221> NAME/KEY: unsure
<222> LOCATION: (415)
<223> OTHER INFORMATION: n = A, C, G or T
<220> FEATURE:
<221> NAME/KEY: unsure
<222> LOCATION: (421)
<223> OTHER INFORMATION: n = A, C, G or T

<400> SEQUENCE: 15
agacattgat atccttgtac actctctcgc caacggtcct gaggtaacaa agtcactgct      60
tgagacatca aggagaggat accttgctgc aatttcagca tctagttatt cttatgtttc     120
tttacttcaa cacttccttc ccataatgaa tccaggaggt gctagtatct ctttgaccta     180
catagcttct gaaaggataa ttcctggcta cggtggtggt atgagttcag caaaagcagc     240
tcttgagagt gatacagatt cttgcatatn aagcaggtcg aaaagcaaa atcagagtga      300 acaccatatc agcaggtcca ttgggaagcc gagcagcaaa agccatggat tnatcgagaa     360
gatgtnggga ttctanggta atgcaccatg gcaaaaggga ntangggcaa anganttggg     420 nac                                                                   423

<210> SEQ ID NO 16
<211> LENGTH: 121
<212> TYPE: PRT
<213> ORGANISM: Zea mays
<220> FEATURE:
<221> NAME/KEY: UNSURE
<222> LOCATION: (90)
<223> OTHER INFORMATION: Xaa = ANY AMINO ACID
<220> FEATURE:
<221> NAME/KEY: UNSURE
<222> LOCATION: (117)
<223> OTHER INFORMATION: Xaa = ANY AMINO ACID

<400> SEQUENCE: 16

Asp Ile Asp Ile Leu Val His Ser Leu Ala Asn Gly Pro Glu Val Thr
  1               5                  10                  15

Lys Ser Leu Leu Glu Thr Ser Arg Arg Gly Tyr Leu Ala Ala Ile Ser
             20                  25                  30

Ala Ser Ser Tyr Ser Tyr Val Ser Leu Leu Gln His Phe Leu Pro Ile
         35                  40                  45

Met Asn Pro Gly Gly Ala Ser Ile Ser Leu Thr Tyr Ile Ala Ser Glu
     50                  55                  60

Arg Ile Ile Pro Gly Tyr Gly Gly Gly Met Ser Ser Ala Lys Ala Ala
 65                  70                  75                  80

Leu Glu Ser Asp Thr Asp Ser Cys Ile Xaa Ser Arg Ser Lys Arg Gln
             85                  90                  95

Asn Gln Ser Glu His His Ile Ser Arg Ser Ile Gly Lys Pro Ser Ser
            100                 105                 110

Lys Ser His Gly Xaa Ile Glu Lys Met
            115                 120

<210> SEQ ID NO 17
<211> LENGTH: 595
<212> TYPE: DNA
<213> ORGANISM: Zea mays
<220> FEATURE:
```

<221> NAME/KEY: unsure
<222> LOCATION: (467)
<223> OTHER INFORMATION: n = A, C, G or T
<220> FEATURE:
<221> NAME/KEY: unsure
<222> LOCATION: (523)
<223> OTHER INFORMATION: n = A, C, G or T
<220> FEATURE:
<221> NAME/KEY: unsure
<222> LOCATION: (587)
<223> OTHER INFORMATION: n = A, C, G or T

<400> SEQUENCE: 17

```
attttggcag cattgacata ctagtgcatt ctcttgctaa tggcccagag gtaacgaagc    60
ctttgttgga aacctcaaga agaggctatc ttgcggcaat ttctgcatcc agttactcct   120
atgtttcatt gcttcagcac ttccttccta taatgaatcc cggtggtgct agcatctctc   180
taacatacat tgcatctgaa agggcgattc ctgggtatgg tggtgggatg agttctgcta   240
aagcagctct tgagagtgat acacgggtgc ttgcattcga agctgggcga aaaggcaaaa   300
tcagagttaa caccatatca gcaggccctc ttgggagccg agctgctaag gcaattggat   360
ttattgagaa gatgatagag tactcatatg ttaatgcacc attgcagaag gagctgttgg   420
ctgatgaggt ggggaacaca gctgcattcc tggtttcttc attggcntct gccatcaacg   480
gctcgactgt ttatgttgac aatgggctca atacaatggg ggntgcaatt gacaagccct   540
acccataacg tcataagatg tggttgtgga gataaacgac ctttccngtg cattc        595
```

<210> SEQ ID NO 18
<211> LENGTH: 181
<212> TYPE: PRT
<213> ORGANISM: Zea mays
<220> FEATURE:
<221> NAME/KEY: UNSURE
<222> LOCATION: (174)
<223> OTHER INFORMATION: Xaa = ANY AMINO ACID

<400> SEQUENCE: 18

```
Phe Gly Ser Ile Asp Ile Leu Val His Ser Leu Ala Asn Gly Pro Glu
  1               5                  10                  15

Val Thr Lys Pro Leu Leu Glu Thr Ser Arg Arg Gly Tyr Leu Ala Ala
             20                  25                  30

Ile Ser Ala Ser Ser Tyr Ser Tyr Val Ser Leu Leu Gln His Phe Leu
         35                  40                  45

Pro Ile Met Asn Pro Gly Gly Ala Ser Ile Ser Leu Thr Tyr Ile Ala
     50                  55                  60

Ser Glu Arg Ala Ile Pro Gly Tyr Gly Gly Gly Met Ser Ser Ala Lys
 65                  70                  75                  80

Ala Ala Leu Glu Ser Asp Thr Arg Val Leu Ala Phe Glu Ala Gly Arg
                 85                  90                  95

Lys Gly Lys Ile Arg Val Asn Thr Ile Ser Ala Gly Pro Leu Gly Ser
            100                 105                 110

Arg Ala Ala Lys Ala Ile Gly Phe Ile Glu Lys Met Ile Glu Tyr Ser
        115                 120                 125

Tyr Val Asn Ala Pro Leu Gln Lys Glu Leu Leu Ala Asp Glu Val Gly
    130                 135                 140

Asn Thr Ala Ala Phe Leu Val Ser Ser Leu Ala Ser Ala Ile Asn Gly
145                 150                 155                 160

Ser Thr Val Tyr Val Asp Asn Gly Leu Asn Thr Met Gly Xaa Ala Ile
                165                 170                 175
```

Asp Lys Pro Tyr Pro
              180

<210> SEQ ID NO 19
<211> LENGTH: 513
<212> TYPE: DNA
<213> ORGANISM: Zea mays
<220> FEATURE:
<221> NAME/KEY: unsure
<222> LOCATION: (384)
<223> OTHER INFORMATION: n = A, C, G or T
<220> FEATURE:
<221> NAME/KEY: unsure
<222> LOCATION: (428)
<223> OTHER INFORMATION: n = A, C, G or T
<220> FEATURE:
<221> NAME/KEY: unsure
<222> LOCATION: (454)
<223> OTHER INFORMATION: n = A, C, G or T
<220> FEATURE:
<221> NAME/KEY: unsure
<222> LOCATION: (463)
<223> OTHER INFORMATION: n = A, C, G or T
<220> FEATURE:
<221> NAME/KEY: unsure
<222> LOCATION: (491)
<223> OTHER INFORMATION: n = A, C, G or T
<220> FEATURE:
<221> NAME/KEY: unsure
<222> LOCATION: (493)
<223> OTHER INFORMATION: n = A, C, G or T
<220> FEATURE:
<221> NAME/KEY: unsure
<222> LOCATION: (500)
<223> OTHER INFORMATION: n = A, C, G or T
<220> FEATURE:
<221> NAME/KEY: unsure
<222> LOCATION: (502)
<223> OTHER INFORMATION: n = A, C, G or T

<400> SEQUENCE: 19
aggcaccact cgcatcgtgt gctcagtcag atccccgtcc cgcatttcct aaggccaggt      60
tagttggcat tgaagacgat gactgcttct gcagctgctg gtgtgcagat ggtggctgca     120
cgcccttgca tttcggcctc gccaggaatt cttaccgcac gggtttctag gactgattgc     180
atgctcagta ccactgctac attccccaaa atcagctgct cctggcctct aaggtttaag     240
cgcaatgatg ttgttgtaag agcaatatcg aagagtgtg gcccgcaggg gcttcccatt      300
gatctcagag gtaaaagggc attcattgct ggagttgctg atgataatgg ctatggatgg     360
gcaattgcga aggcacttgc tgcnggctgg gtgctgaaat tcttgtgggg tacatgggtg     420
ccggcacnta acataatttg gacaagtcc tganggcgtg ggnaagtttg datgaagcac      480
ggggagctgg nangatgggn tngcggggg ggg                                   513

<210> SEQ ID NO 20
<211> LENGTH: 124
<212> TYPE: PRT
<213> ORGANISM: Zea mays
<220> FEATURE:
<221> NAME/KEY: UNSURE
<222> LOCATION: (117)
<223> OTHER INFORMATION: Xaa = ANY AMINO ACID

<400> SEQUENCE: 20

Met Thr Ala Ser Ala Ala Ala Gly Val Gln Met Val Ala Ala Arg Pro
 1               5                  10                  15

Cys Ile Ser Ala Ser Pro Gly Ile Leu Thr Ala Arg Val Ser Arg Thr
            20                  25                  30

-continued

```
Asp Cys Met Leu Ser Thr Thr Ala Thr Phe Pro Lys Ile Ser Cys Ser
        35                  40                  45

Trp Pro Leu Arg Phe Lys Arg Asn Asp Val Val Arg Ala Ile Ser
    50                  55                  60

Glu Glu Cys Gly Pro Gln Gly Leu Pro Ile Asp Leu Arg Gly Lys Arg
65                  70                  75                  80

Ala Phe Ile Ala Gly Val Ala Asp Asp Asn Gly Tyr Gly Trp Ala Ile
                85                  90                  95

Ala Lys Ala Leu Ala Ala Gly Trp Val Leu Lys Phe Leu Trp Gly Thr
               100                 105                 110

Trp Val Pro Ala Xaa Asn Ile Ile Trp Asp Lys Ser
               115                 120

<210> SEQ ID NO 21
<211> LENGTH: 13
<212> TYPE: PRT
<213> ORGANISM: Conserved Sequence Motif

<400> SEQUENCE: 21

Pro Gly Tyr Gly Gly Gly Met Asn Ala Ala Lys Ala Ala
1               5                   10
```

ENOYL-ACP REDUCTASES

This application claims the benefit of U.S. Provisional Application No. 60/303,309, filed 6 Jul. 2001. The entire content of the provisional application is herein incorporated by reference.

FIELD OF THE INVENTION

This invention is in the field of plant molecular biology. More specifically, this invention pertains to nucleic acid fragments encoding corn (*Zea maize*), rice (*Oryza sativa*), and soybean (*Glycine max*) enoyl-ACP reductases in plants and seeds.

BACKGROUND OF THE INVENTION

Fatty acid biosynthesis in plants takes place in plastids, and closely resembles that in bacteria. The process mainly involves cyclic reactions that incorporate two-carbon units into a growing acyl chain. In the last few steps of the fatty acid synthesis cycle, a 3-ketoacyl substrate is reduced to yield a fully saturated acyl chain. The final reduction step in the process is catalyzed by enoyl-ACP reductase which converts the 2,3-trans-enoyl-ACP to the corresponding saturated acyl-ACP.

Fatty acid synthesis is an important metabolic pathway, since fatty acids are essential components of plant membranes and seed oils, among others. The fatty acid composition of plant membranes is thought to be an important factor in responding to environmental stress. Accordingly the availability of nucleotide sequences encoding enoyl-ACP reductase provides a means to manipulate fatty acid composition, and consequently, to improve plant response to stress and seed oil composition, both of which are important agronomic characteristics.

Since fatty acids are essential to plant growth and development, inhibiting enoyl-ACP reductase can lead to inhibition of plant growth and development. Indeed, Arabidopsis plants with a defective enoyl-ACP reductase gene exhibit premature cell death and dramatic alterations in plant morphology which include chlorotic and curly leaves, distorted siliques, premature senescence of primary inflorescences, reduced fertility, and semidwarfism (Mou et al. (2000) *Plant Cell* 12:405–417). Also, the antibacterial compound triclosan and the antitubercular drug isoniazid have enoyl-ACP reductase as their molecular target (Blanchard (1996) *Annu. Rev. Biochem.* 65:215–239; Suguna et al. (2001) *Biochem. Biophys. Res. Commun.* 283:224–228). Accordingly, the nucleotide sequences disclosed herein provide a starting point for herbicide and fungicide discovery and design.

SUMMARY OF THE INVENTION

The present invention concerns isolated polynucleotides comprising a nucleotide sequence encoding a polypeptide having enoyl-ACP reductase activity wherein the amino acid sequence of the polypeptide and the amino acid sequence of SEQ ID NO:2 or 8 have at least 86% sequence identity. It is preferred that the identity be at least 90%, it is preferable if the identity is at least 95%. The present invention also relates to isolated polynucleotides comprising the complement of the nucleotide sequence. More specifically, the present invention concerns isolated polynucleotides encoding the polypeptide sequence of SEQ ID NO:2 or 8 or nucleotide sequences comprising the nucleotide sequence of SEQ ID NO:1 or 7.

In a first embodiment, the present invention relates to an isolated polynucleotide comprising: (a) a nucleotide sequence encoding a polypeptide having enoyl-ACP reductase activity, wherein the amino acid sequence of the polypeptide and the amino acid sequence of SEQ ID NO:2 or 8 have at least 86%, 90%, or 95% identity, or (b) the complement of the nucleotide sequence of (a). The polypeptide preferably comprises the amino acid sequence of SEQ ID NO:2 or 8. The nucleotide sequence preferably comprises the nucleotide sequence of SEQ ID NO:1 or 7.

In a second embodiment, the present invention concerns a recombinant DNA construct comprising any of the isolated polynucleotides of the present invention operably linked to at least one regulatory sequence, and a cell, a plant, and a seed comprising the recombinant DNA construct.

In a third embodiment, the present invention relates to a vector comprising any of the isolated polynucleotides of the present invention.

In a fourth embodiment, the present invention concerns a method for transforming a cell comprising transforming a cell with any of the isolated polynucleotides of the present invention, and the cell transformed by this method. Advantageously, the cell is eukaryotic, e.g., a yeast or plant cell, or prokaryotic, e.g., a bacterium.

In a fifth embodiment, the present invention relates to a method for producing a transgenic plant comprising transforming a plant cell with any of the isolated polynucleotides of the present invention and regenerating a plant from the transformed plant cell. The invention is also directed to the transgenic plant produced by this method, and seed obtained from this transgenic plant.

In a sixth embodiment, the present invention concerns an isolated polypeptide having enoyl-ACP reductase activity, wherein the amino acid sequence of the polypeptide and the amino acid sequence of SEQ ID NO:2 or 8 have at least 86%, 90%, or 95% identity. The amino acid sequence preferably comprises the amino acid sequence of SEQ ID NO:2 or 8.

In a seventh embodiment, the present invention relates to a method for isolating a polypeptide encoded by the polynucleotide of the present invention comprising isolating the polypeptide from a cell containing a recombinant DNA construct comprising the polynucleotide operably linked to at least one regulatory sequence.

In an eight embodiment, the invention concerns a method for positive selection of a transformed cell comprising: (a) transforming a host cell with the recombinant DNA construct of the present invention or an expression cassette of the present invention; and (b) growing the transformed host cell, preferably a plant cell, such as a monocot or a dicot, under conditions which allow expression of the enoyl-ACP reductase polynucleotide in an amount sufficient to complement a null mutant to provide a positive selection means.

In a ninth embodiment, this invention relates to a method of altering the level of expression of an enoyl-ACP reductase in a host cell comprising: (a) transforming a host cell with a recombinant DNA construct of the present invention; and (b) growing the transformed host cell under conditions that are suitable for expression of the recombinant DNA construct wherein expression of the recombinant DNA construct results in production of altered levels of the enoyl-ACP reductase in the transformed host cell when compared to a non-transformed cell.

A further embodiment of the instant invention is a method for evaluating at least one compound for its ability to inhibit the activity of an enoyl-ACP reductase, the method comprising the steps of: (a) introducing into a host cell a recombinant DNA construct comprising a nucleic acid fragment encoding an enoyl-ACP reductase polypeptide, operably linked to at least one regulatory sequence; (b) growing the host cell under conditions that are suitable for expression of the recombinant DNA construct wherein expression of the recombinant DNA construct results in production of an enoyl-ACP reductase polypeptide in the host cell; (c) optionally purifying the enoyl-ACP reductase polypeptide expressed by recombinant DNA construct in the host cell; (d) treating the enoyl-ACP reductase polypeptide with a compound to be tested; and (e) comparing the activity of the enoyl-ACP reductase polypeptide that has been treated with a test compound to the activity of an untreated enoyl-ACP reductase polypeptide, and selecting compounds with potential for inhibitory activity.

BRIEF DESCRIPTION OF THE DRAWINGS AND SEQUENCE LISTINGS

The invention can be more fully understood from the following detailed description and the accompanying drawings and Sequence Listing which form a part of this application.

FIG. 1A through FIG. 1C show an alignment of the amino acid sequences encoded by corn clone csh1c.pk001.e18:fis (SEQ ID NO:2); rice clone rca1n.pk023.j4:fis (SEQ ID NO:4); and soybean clone sdp3c.pk018.e20:fis (SEQ ID NO:8) with the amino acid sequences for enoyl-ACP reductase from *oryza sativa* (having NCBI General Identifier No. 7489537; SEQ ID NO:11) and *Nicotiana tabacum* (having NCBI General Identifier No. 7489119; SEQ ID NO:12). Amino acids conserved among all sequences are indicated by an asterisk (*) above the alignment. The conserved motif characteristic of enoyl-ACP reductases is written in white and boxed in black. The program uses dashes to maximize the alignment. FIG. 1A shows the alignment of amino acids 1 through 180; FIG. 1B shows the alignment of amino acids 181 through 360; and FIG. 1C shows the alignment of amino acids 361 through 402.

FIG. 2 shows the relative expression levels of the enoyl-ACP reductases encoded by corn clones cc71se-b.pk0013.e10 (SEQ ID NO:14); ceb1.pk0042.c2 (SEQ ID NO:16); ceb1.pk0046.c6 (SEQ ID NO:18); and cho1c.pk002.f13 (SEQ ID NO:20). The developmental stages are numbered on the X axis with 1 through 8 corresponding to embryos harvested at 10, 15, 20, 25, 30, 35, 40, and 45 days after pollination (dap), 9 corresponding to the stem of a 2 week-old seedling, and 10 corresponding to the mature tassle.

Table 1 lists the polypeptides that are described herein, the plant from which the polynucleotides are derived, the designation of the cDNA clones that comprise the nucleic acid fragments encoding polypeptides representing all or a substantial portion of these polypeptides, and the corresponding identifier (SEQ ID NO☺ as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Enoyl-ACP Reductases

| | | SEQ ID NO: | |
|---|---|---|---|
| Plant | Clone Designation | (Nucleotide) | (Amino Acid) |
| Corn | csh1c.pk001.e18:fis | 1 | 2 |
| Rice | rca1n.pk023.j4:fis | 3 | 4 |
| Rice | rsl1n.pk005.c14 | 5 | 6 |
| Soybean | sdp3c.pk018.e20:fis | 7 | 8 |
| Wheat | wl1n.pk0141.g8 | 9 | 10 |
| Rice | NCBI gi 7489537 | | 11 |
| Tobacco | NCBI gi 7489119 | | 12 |
| Corn | cc71se-b.pk0013.e10 | 13 | 14 |
| Corn | ceb1.pk0042.c2 | 15 | 16 |
| Corn | ceb1.pk0046.c6 | 17 | 18 |
| Corn | cho1c.pk002.f13 | 19 | 20 |
| Conserved Motif | | | 21 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

The problem to be solved, therefore, was to identify polynucleotides that encode enoyl-ACP reductase proteins. These polynucleotides may be used in plant cells to alter fatty acid biosynthesis. More specifically, the polynucleotides of the instant invention may be used to create transgenic plants where the enoyl-ACP reductase levels are altered with respect to non-transgenic plants which would result in plants with a certain phenotype. Overexpression of enoyl-ACP reductase should result in plants with higher resistance to stress. Furthermore, enoyl-ACP reductases are not found in eukaryotic organisms making polypeptides encoding enoyl-ACP reductase an attractive target for the design of novel anti-fungal and herbicidal agents. Accordingly, the availability of nucleic acid sequences encoding all or a portion of an enoyl-ACP reductase will facilitate studies to better understand the effects of stress on lipids. The present invention has solved this problem by providing polynucleotide and deduced polypeptide sequences corresponding to novel enoyl-ACP reductases from corn (*Zea mays*) and soybean (*Glycine max*).

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least 30 contiguous nucleotides, preferably at least 40 contiguous nucleotides, most preferably at least 60 contiguous nucleotides derived from SEQ ID NO:1 or 7, or the complement of such sequences.

The term "isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques. A "recombinant DNA construct" comprises any of the isolated polynucleotides of the present invention operably linked to at least one regulatory sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-á-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides, preferably at least 40 contiguous nucleotides, most preferably at least 60 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 30 (preferably at least 40, most preferably at least 60) contiguous nucleotides derived from a nucleotide sequence of SEQ ID NO:1 or 7, and the complement of such nucleotide sequences may be used to alter the expression and/or function of an enoyl-ACP reductase in a host cell. A method of using an isolated polynucleotide to alter the level of expression of a polypeptide in a host cell (eukaryotic, such as plant or yeast, prokaryotic such as bacterial) may comprise the steps of: constructing an isolated polynucleotide of the present invention or an isolated recombinant DNA construct of the present invention; introducing the isolated polynucleotide or the isolated recombinant DNA construct into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are at least about 86% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above identities but typically encode a polypeptide having at least about 50 amino acids, preferably at least about 100 amino acids, more preferably at least about 150 amino acids, still more preferably at least about 200 amino acids, and most preferably at least about 250 amino acids.

It is well understood by one skilled in the art that many levels of sequence identity are useful in identifying related polypeptide sequences. Useful examples of percent identities are about 50%, about 55%, about 60%, about 65%, about 70%, about 75%, about 80%, about 85%, about 90%, about 95%, or any integer percentage from 55% to 100%. Sequence alignments and percent identity calculations were performed using the Megalign program of the LASER-GENE bioinformatics computing suite (DNASTAR Inc., Madison, Wis.). Multiple alignment of the sequences was performed using the ClustalV method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410; see also the explanation of the BLAST alogarithm on the world wide web site for the National Center for Biotechnology Information at the National Library of Medicine of the National Institutes of Health). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign-gene" refers to a gene not normally found in the host organism, but that is introduced into the host organism by gene transfer. Foreign genes can comprise native genes inserted into a non-native organism, recombinant DNA constructs, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

"3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277; Ishida Y. et al. (1996) *Nature Biotech.* 14:745–750) and particle-accelerated or "gene gun" transformation technology (Klein et al. (1987) *Nature (London)* 327:70–73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms. The term "transformation" as used herein refers to both stable transformation and transient transformation.

The terms "recombinant construct", "expression construct" and "recombinant expression construct" are used interchangeably herein. These terms refer to a functional unit of genetic material that can be inserted into the genome of a cell using standard methodology well known to one skilled in the art. Such construct may be used by itself or may be used in conjunction with a vector. If a vector is used, the choice of vector is dependent upon the method that will be used to transform host plants as is well known to those skilled in the art.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

"Motifs" or "subsequences" refer to short regions of conserved sequences of nucleic acids or amino acids that comprise part of a longer sequence. For example, it is expected that such conserved subsequences would be important for function, and could be used to identify new homologues in plants. It is expected that some or all of the elements may be found in a homologue. Also, it is expected that one or two of the conserved amino acids in any given motif may differ in a true homologue.

"PCR" or "polymerase chain reaction" is well known by those skilled in the art as a technique used for the amplification of specific DNA segments (U.S. Pat. Nos. 4,683,195 and 4,800,159).

The present invention concerns isolated polynucleotides comprising a nucleotide sequences encoding enoyl-ACP reductase polypeptides having at least 86% identity, based on the ClustaVI method of alignment, when compared to a polypeptide of SEQ ID NO:2 or 8. This invention also relates to the isolated complement of such polynucleotides, wherein the complement and the polynucleotide consist of the same number of nucleotides, and the nucleotide sequences of the complement and the polynucleotide have 100% complementarity.

Nucleic acid fragments encoding at least a portion of several enoyl-ACP reductases have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other enoyl-ACP reductases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least 30

(preferably at least 40, most preferably at least 60) contiguous nucleotides derived from a nucleotide sequence of SEQ ID NOs:1 or 7 and the complement of such nucleotide sequences may be used in such methods to obtain a nucleic acid fragment encoding a substantial portion of an amino acid sequence of a polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

In another embodiment, this invention concerns viruses and host cells comprising either the recombinant DNA constructs of the invention as described herein or isolated polynucleotides of the invention as described herein. Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the level of lipids in those cells. Overexpression of the polypeptides of the present invention should allow the transgenic plants to resist stress. Because enoyl-ACP reductases are not present in eukaryotes, the polynucleotides of the present invention will be useful for the identification of anti-fungal and herbicidal agents.

Overexpression of the proteins of the instant invention may be accomplished by first constructing a recombinant DNA construct in which the coding region is operably linked to a promoter capable of directing expression of a gene in the desired tissues at the desired stage of development. The recombinant DNA construct may comprise promoter sequences and translation leader sequences derived from the same genes. 3' Non-coding sequences encoding transcription termination signals may also be provided. The instant recombinant DNA construct may also comprise one or more introns in order to facilitate gene expression.

Plasmid vectors comprising the instant isolated polynucleotide(s) (or recombinant DNA construct(s)) may be constructed. The choice of plasmid vector is dependent upon the method that will be used to transform host plants. The skilled artisan is well aware of the genetic elements that must be present on the plasmid vector in order to successfully transform, select and propagate host cells containing the recombinant DNA construct or chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate their secretion from the cell. It is thus envisioned that the recombinant DNA construct(s) described above may be further supplemented by directing the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a recombinant DNA construct designed for co-suppression of the instant polypeptide can be constructed by linking a gene or gene fragment encoding that polypeptide to plant promoter sequences. Alternatively, a recombinant DNA construct designed to express antisense RNA for all or part of the instant nucleic acid fragment can be constructed by linking the gene or gene fragment in reverse orientation to plant promoter sequences. Either the co-suppression or antisense recombinant DNA constructs could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different recombinant DNA constructs utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention concerns an enoyl-ACP reductase polypeptide having an amino acid sequence that is at least 86% identical, based on the ClustalV method of alignment, to a polypeptide of SEQ ID NO:2 or 8.

The instant polypeptides (or portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a recombinant DNA construct for production of the instant polypeptides. This recombinant DNA construct could then be introduced into appropriate microorganisms via transformation to provide high level expression of the encoded enoyl-ACP reductase. An example of a vector for high level expression of the instant polypeptides in a bacterial host is provided (Example 6).

Additionally, the instant polypeptides can be used as a target to facilitate design and/or identification of inhibitors of those enzymes that may be useful as herbicides. This is desirable because the polypeptides described herein catalyze the last few steps of fatty acid synthesis. Accordingly, inhibition of the activity of one or more of the enzymes described herein could lead to inhibition of plant growth. Thus, the instant polypeptides could be appropriate for new herbicide discovery and design.

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

Nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several kb to several hundred kb; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries; Isolation and Sequencing of cDNA Clones cDNA libraries representing mRNAs from various corn, rice, soybean, and wheat tissues were prepared. The characteristics of the libraries are described below.

TABLE 2 cDNA Libraries from Corn, Rice, Soybean, and Wheat

| Library | Tissue | Clone |
| --- | --- | --- |
| csh1c | Corn Shoots and Roots Sprayed with Acetone | csh1c.pk001.e18 |
| rca1n | Rice Callus* | rca1n.pk023.j4 |
| rsl1n | Rice 15-Day-Old Seedling* | rsl1n.pk005.c14 |
| sdp3c | Soybean Developing Pod (8–9 mm) | sdp3c.pk018.e20 |
| wl1n | Wheat Leaf From 7 Day Old Seedling Light Grown* | wl1n.pk0141.g8 |
| cc71se-b | Corn Callus Type II Tissue, Somatic Embryo Formed | cc71se-b.pk0013.e10 |
| ceb1 | Corn Embryo 10 to 11 Days After Pollination | ceb1.pk0042.c2 |
| ceb1 | Corn Embryo 10 to 11 Days After Pollination | ceb1.pk0046.c6 |
| cho1c | Corn Embryo 20 Days After Pollination | cho1c.pk002.f13 |

*This library was normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) Science 252:1651–1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the Saccharomyces cerevisiae Ty1 transposable element (Devine and Boeke (1994) Nucleic Acids Res. 22:3765–3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) Nucleic Acids Res. 11:5147–5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred/Phrap (P. Green, University of Washington, Seattle). Phred/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

In some of the clones the cDNA fragment corresponds to a portion of the 3'-terminus of the gene and does not cover the entire open reading frame. In order to obtain the upstream information one of two different protocols are used. The first of these methods results in the production of a fragment of DNA containing a portion of the desired gene sequence while the second method results in the production of a fragment containing the entire open reading frame. Both of these methods use two rounds of PCR amplification to obtain fragments from one or more libraries. The libraries some times are chosen based on previous knowledge that the specific gene should be found in a certain tissue and some times are randomly-chosen. Reactions to obtain the same gene may be performed on several libraries in parallel or on a pool of libraries. Library pools are normally prepared using from 3 to 5 different libraries and normalized to a uniform dilution. In the first round of amplification both methods use a vector-specific (forward) primer corresponding to a portion of the vector located at the 5'-terminus of the clone coupled with a gene-specific (reverse) primer. The first method uses a sequence that is complementary to a portion of the already known gene sequence while the second method uses a gene-specific primer complementary to a portion of the 3'-untranslated region (also referred to as UTR). In the second round of amplification a nested set of primers is used for both methods. The resulting DNA fragment is ligated into a pBluescript vector using a commercial kit and following the manufacturer's protocol. This kit is selected from many available from several vendors including Invitrogen (Carlsbad, Calif.), Promega Biotech (Madison, Wis.), and Gibco-BRL (Gaithersburg, Md.). The plasmid DNA is isolated by alkaline lysis method and submitted for sequencing and assembly using Phred/Phrap, as above.

Example 2

Identification of cDNA Clones cDNA clones encoding enoyl-ACP reductases were identified by conducting BLAST (Basic Local Alignment Search Tool; Altschul et al. (1993) *J. Mol. Biol.* 215:403–410; see also the explanation of the BLAST alogarithm on the world wide web site for the National Center for Biotechnology Information at the National Library of Medicine of the National Institutes of Health) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the genbank database as described above. ESTs that contain sequences more 5- or 3-prime can be found by using the BLASTn algorithm (Altschul et al (1997) *Nucleic Acids Res.* 25:3389–3402.) against the Du Pont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 1. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 3

Characterization of cDNA Clones Encoding Enoyl-ACP Reductases

The BLASTX search using the EST sequences from clones listed in Table 3 revealed similarity of the polypeptides encoded by the cDNAs to enoyl-ACP reductase (NADPH) from *Oryza sativa* or *Nicotiana tabacum* (NCBI General Identifier Nos. SEQ ID NO:11 and 7489119, respectively). Shown in Table 3 are the BLAST results for individual ESTs ("EST"), or the sequences of the entire cDNA inserts comprising the indicated cDNA clones ("FIS") encoding an entire protein ("CGS"):

TABLE 3

BLAST Results for Sequences Encoding Polypeptides Homologous to Enoyl-ACP Reductase

| Clone | Status | NCBI GI No. | BLAST pLog Score |
|---|---|---|---|
| csh1c.pk001.e18:fis | CGS | 7489537 | 177.00 |
| rca1n.pk023.j4:fis | CGS | 7489537 | >180.00 |
| rsl1n.pk005.c14 | EST | 7489537 | 10.52 |
| sdp3c.pk018.e20:fis | CGS | 7489119 | 166.00 |
| wl1n.pk0141.g8 | EST | 7489537 | 28.70 |

The nucleotide sequence of the entire cDNA insert in clone csh1c.pk001.e18 is shown in SEQ ID NO:1; the deduced amino acid sequence from nucleotides 54 through 1166 of SEQ ID NO:1 is shown in SEQ ID NO:2. The nucleotide sequence of the entire cDNA insert in clone rca1n.pk023.j4 is shown in SEQ ID NO:3; the deduced amino acid sequence from nucleotides 175 through 1299 of SEQ ID NO:3 is shown in SEQ ID NO:4. The nucleotide sequence of a portion of the cDNA insert in clone rsl1n.pk005.c14 is shown in SEQ ID NO:5; the deduced amino acid sequence from nucleotides 26 through 232 of SEQ ID NO:5 is shown in SEQ ID NO:6. The nucleotide sequence of the entire cDNA insert in clone sdp3c.pk018.e20 is shown in SEQ ID NO:7; the deduced amino acid sequence from nucleotides 47 through 1253 is shown in SEQ ID NO:8. The nucleotide sequence of a portion of the cDNA insert in clone wl1n.pk0141.g8 is shown in SEQ ID NO:9; the deduced amino acid sequence from nucleotides 1 through 474 of SEQ ID NO:9 is shown in SEQ ID NO:10.

FIG. 1A through FIG. 1C present an alignment of the amino acid sequences set forth in SEQ ID NOs:2, 4, and 8 with the *Oryza sativa* and *Nicotiana tabacum* enoyl-ACP reductase sequences (SEQ ID NO:11 and SEQ ID NO:12, respectively). The Tyr and Lys residues separated by seven amino acids and considered to be characteristic of enoyl-ACP reductases are found in a conserved motif (Parikh et al. (1999) *Biochemistry* 38:13623–13634) which is written in white and boxed in black in the figure. According Parikh et al. this motif is found at amino acids 262 through 274 of the rice sequence (SEQ ID NO:11) and consists of Pro Gly Tyr Gly Gly Gly Met Asn Ala Ala Lys Ala Ala (SEQ ID NO:21). This motif is 100% identical in SEQ ID NO:2, SEQ ID NO:4, and SEQ ID NO:8. It is found at amino acids 258 through 270 of SEQ ID NO:2, amino acids 262 through 274 of SEQ ID NO:4, and amino acids 272 through 284 of SEQ ID NO:8. Amino acids conserved among all sequences are indicated by an asterisk above the alignment. The program uses dashes to maximize the alignment.

Further sequencing and searching of the DuPont proprietary database allowed the identification of other corn clones encoding enoyl-ACP reductases. These clones were used in analyses of developmental accumulation of enoyl-ACP reductases in corn. The BLASTX search using the EST sequences from clones listed in Table 4 revealed similarity of the polypeptides encoded by the cDNAs to enoyl-ACP reductase from *Oryza sativa* (NCBI General Identifier No.

7489537) and *Brassica napus* (NCBI General Identifier No. 14422257). Shown in Table 4 are the BLAST results for individual ESTs ("EST"):

TABLE 4

BLAST Results for Sequences Encoding Polypeptides Homologous to Enoyl-ACP Reductase

| Clone | Status | NCBI GI No. | BLAST pLog Score |
|---|---|---|---|
| cc71se-b.pk0013.e10 | EST | 7489537 | 45.22 |
| ceb1.pk0042.c2 | EST | 14422257 | 41.70 |
| ceb1.pk0046.c6 | EST | 7489537 | 84.40 |
| cho1c.pk002.f13 | EST | 7489537 | 34.15 |

The nucleotide sequence of a portion of the cDNA insert in clone cc71se-b.pk0013.e10 is shown in SEQ ID NO:13; the deduced amino acid sequence from nucleotides 3 through 329 of SEQ ID NO:13 is shown in SEQ ID NO:14. The nucleotide sequence of a portion of the cDNA insert in clone ceb1.pk0042.c2 is shown in SEQ ID NO:15; the deduced amino acid sequence from nucleotides 2 through 364 of SEQ ID NO:15 is shown in SEQ ID NO:16. The nucleotide sequence of a portion of the cDNA insert in clone ceb1.pk0046.c6 is shown in SEQ ID NO:17; the deduced amino acid sequence from nucleotides 3 through 545 of SEQ ID NO:17 is shown in SEQ ID NO:18. The nucleotide sequence of a portion of the cDNA insert in clone cho1c.pk002.f13 is shown in SEQ ID NO:19; the deduced amino acid sequence from nucleotides 79 through 450 of SEQ ID NO:19 is shown in SEQ ID NO:20.

A graphical representation of expression analysis of these four corn ESTs is shown in FIG. 2. The developmental stages are numbered in the X axis with 1 through 8 corresponding to embryos harvested at 10, 15, 20, 25, 30, 35, 40, and 45 days after pollination (dap), 9 corresponding to the stem of a 2 week-old seedling, and 10 corresponding to the mature tassle. FIG. 2 shows enoyl-ACP reductase is expressed throughout development with a dramatic increase in expression at 15 dap.

The data in Table 5 represents a calculation of the percent identity of the amino acid sequences set forth in SEQ ID NOs: 2, 4, 6, 8, 10, 14, 16, 18, and 20 with the *Oryza sativa* enoyl-ACP reductase sequence having NCBI General Identifier No. SEQ ID NO:11 (SEQ ID NO:1 1) and the *Nicotiana tabacum* enoyl-ACP reductase sequence having NCBI General Identifier No. SEQ ID NO:12(SEQ ID NO:12).

TABLE 5

Percent Identity of Amino Acid Sequences Deduced From the Nucleotide Sequences of cDNA Clones Encoding Polypeptides Homologous to Enoyl-ACP Reductase

| | | Percent Identity to | |
|---|---|---|---|
| Clone | SEQ ID NO. | 7489537 | 7489119 |
| csh1c.pk001.e18:fis | 2 | 85.4 | 73.0 |
| rca1n.pk023.j4:fis | 4 | 97.1 | 70.9 |
| rsl1n.pk005.c14 | 6 | 44.9 | 40.6 |
| sdp3c.pk018.e20:fis | 8 | 66.8 | 75.5 |
| wl1n.pk0141.g8 | 10 | 46.2 | 41.1 |
| cc71se-b.pk001.e10 | 14 | 89.0 | 80.7 |
| ceb1.pk0042.c2 | 16 | 66.1 | 67.8 |
| ceb1.pk0046.c6 | 18 | 89.5 | 85.6 |
| cho1c.pk002.f13 | 20 | 60.5 | 39.5 |

Sequence alignments and percent identity calculations were performed using the Megalign program of the LASER-GENE bioinformatics computing suite (DNASTAR Inc., Madison, Wis.). Multiple alignment of the sequences was performed using the ClustalV method of alignment (Higgins and Sharp (1989) *CABIOS*. 25 5:151–153) with the default parameters (GAP PENALTY=10, GAP LENGTH PENALTY=10). Default parameters for pairwise alignments using the ClustalI method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode entire corn, rice, and soybean enoyl-ACP reductases and a substantial portion of four corn, one rice, and one wheat enoyl-ACP reductases.

Example 4

Expression of Recombinant DNA Constructs in Monocot Cells

A recombinant DNA construct comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110–2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (*Epicurian Coli* XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a recombinant DNA construct encoding, in the 5' to 3' direction, the maize 27 kD zein promoter, a cDNA fragment encoding the instant polypeptides, and the 10 kD zein 3' region.

The recombinant DNA construct described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from cauliflower mosaic virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 µm in diameter) are coated with DNA using the following technique. Ten pig of plasmid DNAs are added to 50 µL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains bialophos (5 mg per liter) and lacks casein or proline. The tissue continues to grow slowly on this medium. After an additional 2 weeks the tissue can be transferred to fresh N6 medium containing bialophos. After 6 weeks, areas of about 1 cm in diameter of actively growing callus can be identified on some of the plates containing the bialophos-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 5

Expression of Recombinant DNA Constructs in Dicot Cells

A seed-specific expression cassette composed of the promoter and transcription terminator from the gene encoding the D subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites NcoI (which includes the ATG translation initiation codon), SmaI, KpnI and XbaI. The entire cassette is flanked by HindIII sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from cauliflower mosaic virus (Odell et al. (1985) *Nature* 313:810–812), the hygromycin phosphotransferase gene from plasmid pJR225 (from *E. coli*; Gritz et al. (1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µL spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Recombinant DNA Constructs in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoRI and HindIII sites in pET-3a at their original positions. An oligonucleotide adaptor containing EcoRI and Hind III sites was inserted at the BamHI site of pET-3a. This created pET-3aM with additional unique cloning sites for insertion of genes into the expression vector. Then, the NdeI site at the position of translation initiation was converted to an NcoI site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 µg/ml ethidium bromide for visualization of the DNA fragment. The fragment can then be purified from the agarose gel by digestion with GELase™ (Epicentre Technologies, Madison, Wis.) according to the manufacturer's instructions, ethanol precipitated, dried and resuspended in 20 µL of water. Appropriate oligonucleotide adapters may be ligated to the fragment using T4 DNA ligase (New England Biolabs (NEB), Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21 (DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Example 7

Evaluating Compounds for Their Ability to Inhibit the Activity of Enoyl-ACP Reductases The polypeptides described herein may be produced using any number of methods known to those skilled in the art. Such methods include, but are not limited to, expression in bacteria as described in Example 6, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. For example, assays for enoyl-ACP reductase are presented by Slabas et al. (1986) Biochim. Biophys. Acta 877:271–280, and Mou et al. (2000) Plant Cell 12:405–417.

Example 8

Expression of Recombinant DNA Constructs in Yeast Cells

The polypeptides encoded by the polynucleotides of the instant invention may be expressed in a yeast (Saccharomyces cerevisiae) strain YPH. Plasmid DNA may be used as template to amplify the portion encoding the enoyl-ACP reductase. Amplification may be performed using the GC melt kit (Clontech) with a 1 M final concentration of GC melt reagent and using a Perkin Elmer 9700 thermocycler. The amplified insert may then be incubated with a modified pRS315 plasmid (NCBI General Identifier No. 984798; Sikorski, R. S. and Hieter, P. (1989) Genetics 122:19–27) that has been digested with Not I and Spe I. Plasmid pRS315 has been previously modified by the insertion of a bidirectional gal1/10 promoter between the Xho I and Hind III sites. The plasmid may then be transformed into the YPH yeast strain using standard procedures where the insert recombines through gap repair to form the desired transformed yeast strain (Hua, S. B. et al. (1997) Plasmid 38:91–96).

Yeast cells may be prepared according to a modification of the methods of Pompon et al. (Pompon, D. et al. (1996) Meth. Enz. 272:51–64). Briefly, a yeast colony will be grown overnight (to saturation) in SG (-Leucine) medium at 30° C. with good aeration. A 1:50 dilution of this culture will be made into 500 mL of YPGE medium with adenine supplementation and allowed to grow at 30° C. with good aeration to an OD$_{600}$ of 1.6 (24–30 h). Fifty mL of 20% galactose will be added, and the culture allowed to grow overnight at 30° C. The cells will be recovered by centrifugation at 5,500 rpm for five minutes in a Sorvall GS-3 rotor. The cell pellet resuspended in 500 mL of 0.1 M potassium phosphate buffer (pH 7.0) and then allowed to grow at 30° C. for another 24 hours.

The cells may be recovered by centrifugation as described above and the presence of the polypeptide of the instant invention determined by HPLC/mass spectrometry or any other suitable method.

Example 9

Expression of Recombinant DNA Constructs in Insect Cells

The cDNAs encoding the instant polypeptides may be introduced into the baculovirus genome itself. For this purpose the cDNAs may be placed under the control of the polyhedron promoter, the IE1 promoter, or any other one of the baculovirus promoters. The cDNA, together with appropriate leader sequences is then inserted into a baculovirus transfer vector using standard molecular cloning techniques. Following transformation of E. coli DH5α, isolated colonies are chosen and plasmid DNA is prepared and is analyzed by restriction enzyme analysis. Colonies containing the appropriate fragment are isolated, propagated, and plasmid DNA is prepared for cotransfection.

Spodoptera frugiperda cells (Sf-9) are propagated in ExCell® 401 media (JRH Biosciences, Lenexa, Kans.) supplemented with 3.0% fetal bovine serum. Lipofectin® (50 µL at 0.1 mg/mL, Gibco/BRL) is added to a 50 µL aliquot of the transfer vector containing the toxin gene (500 ng) and linearized polyhedrin-negative AcNPV (2.5 µg, Baculogold® viral DNA, Pharmigen, San Diego, Calif.). Sf-9 cells (approximate 50% monolayer) are co-transfected with the viral DNA/transfer vector solution. The supernatant fluid from the co-transfection experiment is collected at 5 days post-transfection and recombinant viruses are isolated employing standard plaque purification protocols, wherein only polyhedrin-positive plaques are selected (O'Reilly et al. (1992), Baculovirus Expression Vectors: A Laboratory Manual, W. H. Freeman and Company, New York.). Sf-9 cells in 35 mM petri dishes (50% monolayer) are inoculated with 100 µL of a serial dilution of the viral suspension, and supernatant fluids are collected at 5 days post infection. In order to prepare larger quantities of virus for characterization, these supernatant fluids are used to inoculate larger tissue cultures for large-scale propagation of recombinant viruses. Expression of the instant polypeptides encoded by the recombinant baculovirus is confirmed by any of the methods mentioned in Example 7.

What is claimed is:

1. An isolated polynucleotide comprising:
   (a) a nucleotide sequence encoding a polypeptide having enoyl-ACP reductase activity, wherein the amino acid sequence of the polypeptide and the amino acid sequence of SEQ ID NO:2 have at least 90% sequence identity, or
   (b) the complement of the nucleotide sequence of (a).

2. The polynucleotide of claim 1, wherein the amino acid sequence of the polypeptide and the amino acid sequence of SEQ ID NO:2 have at least 95% identity.

3. The polynucleotide of claim 1, wherein the amino acid sequence of the polypeptide comprises the amino acid sequence of SEQ ID NO:2.

4. The polynucleotide of claim 1 wherein the nucleotide sequence comprises the nucleotide sequence of SEQ ID NO:1.

5. A vector comprising the polynucleotide of claim 1.

6. A recombinant DNA construct comprising a nucleotide sequence encoding a polypeptide having enoyl-ACP reductase activity, wherein the amino acid sequence of the polypeptide and the amino acid sequence of SEQ ID NO:2 have at least 90% sequence identity and the nucleotide sequence encodinq the polypeptide is operably linked to at least one regulatory sequence.

7. A method for transforming a cell, comprising transforming a cell with a nucleotide sequence encoding a polypeptide having enoyl-ACP reductase activity, wherein the amino acid sequence of the polypeptide and the amino acid sequence of SEQ ID NO:2 have at least 90% sequence identity.

8. A plant, yeast or bacterial cell comprising the recombinant DNA construct of claim 6.

9. A method for producing a plant comprising transforming a plant cell with a nucleotide sequence encoding a polypeptide having enoyl-ACP reductase activity, wherein the amino acid sequence of the polypeptide and the amino acid sequence of SEQ ID NO:2 have at least 90% sequence identity, and regenerating a plant from the transformed plant cell.

10. A plant comprising the recombinant DNA construct of claim 6.

11. A seed comprising the recombinant DNA construct of claim 6.

* * * * *